(12) United States Patent
Park et al.

(10) Patent No.: US 9,465,989 B2
(45) Date of Patent: Oct. 11, 2016

(54) USER AUTHENTICATION APPARATUS AND METHOD USING MOVEMENT OF PUPIL

(71) Applicant: Hyundai Motor Company, Seoul (KR)

(72) Inventors: Sung Min Park, Seoul (KR); Seok Beom Lee, Seoul (KR); Hee Jin Ro, Seoul (KR); Dong Hee Seok, Seoul (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 428 days.

(21) Appl. No.: 13/958,021

(22) Filed: Aug. 2, 2013

(65) Prior Publication Data

US 2014/0147002 A1 May 29, 2014

(30) Foreign Application Priority Data

Nov. 27, 2012 (KR) ........................ 10-2012-0135337

(51) Int. Cl.
*G06K 9/00* (2006.01)
*G06F 21/32* (2013.01)
*H04L 29/06* (2006.01)
*A61B 3/113* (2006.01)
*G06F 3/01* (2006.01)

(52) U.S. Cl.
CPC ............ *G06K 9/0061* (2013.01); *G06F 21/32* (2013.01); *G06K 9/00335* (2013.01); *A61B 3/113* (2013.01); *G06F 3/013* (2013.01); *G06K 9/00597* (2013.01); *H04L 29/06809* (2013.01)

(58) Field of Classification Search
CPC .................... G06K 9/00597; G06K 9/00604; G06K 9/0061; G06K 9/003353; G06F 3/013; G06F 21/30; G06F 21/32; A61B 3/113; H04L 29/06809

USPC .......................................... 382/115, 117, 107
See application file for complete search history.

(56) References Cited

U.S. PATENT DOCUMENTS

| | | | |
|---|---|---|---|
| 6,421,453 B1 * | 7/2002 | Kanevsky et al. ............. | 382/115 |
| 7,572,008 B2 * | 8/2009 | Elvesjo et al. ................ | 351/206 |
| 2002/0118864 A1 | 8/2002 | Kondo et al. | |
| 2003/0076300 A1 * | 4/2003 | Lauper et al. ................ | 345/158 |
| 2008/0072166 A1 * | 3/2008 | Reddy ...................... | G06T 13/00 715/764 |
| 2011/0169730 A1 * | 7/2011 | Sugihara ................. | G06F 3/013 345/156 |
| 2012/0243729 A1 * | 9/2012 | Pasquero ................ | G06F 3/013 382/103 |
| 2014/0165187 A1 * | 6/2014 | Daesung et al. ................. | 726/19 |
| 2014/0320397 A1 * | 10/2014 | Hennessey et al. .......... | 345/156 |
| 2014/0331315 A1 * | 11/2014 | Birk et al. ...................... | 726/19 |

FOREIGN PATENT DOCUMENTS

| | | | |
|---|---|---|---|
| JP | 2002-259981 A | 9/2002 | |
| JP | 2005-303500 A | 10/2005 | |
| JP | 2006-277396 A | 10/2006 | |

(Continued)

*Primary Examiner* — Michael A Newman
(74) *Attorney, Agent, or Firm* — McDermott Will & Emery LLP

(57) ABSTRACT

A user authentication apparatus and method using movement of a pupil is capable of rapidly and accurately performing authentication with high security by storing the respective frequencies of objects mechanically moving on a screen and security keys corresponding thereto, comparing a frequency detected from movement of a pupil gazing at any object with a frequency of the object, and performing the authentication based on a corresponding security key when the detected frequency is included in a predetermined range.

9 Claims, 4 Drawing Sheets

(56) References Cited

FOREIGN PATENT DOCUMENTS

| JP | 2007-141002 A | 6/2007 |
| KR | 10-0310036 B1 | 9/2001 |
| KR | 10-2003-0028789 A | 4/2003 |
| KR | 10-0646031 B1 | 11/2006 |

* cited by examiner

USER AUTHENTICATION APPARATUS AND METHOD USING MOVEMENT OF PUPIL

CROSS-REFERENCE TO RELATED APPLICATION

This application is based on and claims priority from Korean Patent Application No. 10-2012-0135337, filed on Nov. 27, 2012 in the Korean Intellectual Property Office, the disclosure of which is incorporated herein in its entirety by reference.

BACKGROUND

1. Technical Field

The present disclosure relates to a user authentication apparatus and method using movement of a pupil, and more particularly, to a technology of authenticating a user based on a frequency detected from mechanical movement of a pupil.

2. Background

Conventional user authentication technology has mainly used a primitive authentication scheme of authenticating a user by comparing a password with a preset password when an authentication apparatus receives the password through a keypad from the user.

Recently, technology for identifying and authenticating a user using biological characteristics such as a genetic signature, a fingerprint, a voice, a vein, a face shape, an iris, or the like, has been commercialized.

Particularly, in the future, iris recognizing technology is expected to be mainly used in the field of security due to advantages such as high recognition rate and being substantially of forgery-proof.

Conventional user authentication schemes using iris recognition have an advantage in that security is better compared with password input schemes, such as through a keypad. However, an authentication apparatus used for processing these conventional iris recognition user authentication schemes requires high processing capability in order to process a large amount of data. As such, it is difficult to popularize conventional iris recognition user authentication schemes.

Therefore, a method capable of improving security over password input schemes, and capable of rapidly and accurately authenticating a user even with a small data throughput is desired.

SUMMARY

The present disclosure solves the above-mentioned problems occurring in conventional iris recognition technology while advantages achieved by the prior art are maintained intact.

One subject to be achieved by the present disclosure is to provide a user authentication apparatus and method using movement of a pupil capable of rapidly and accurately performing authentication with high security by storing the respective frequencies of objects mechanically moving on a screen and security keys corresponding thereto, comparing a frequency detected from movement of a pupil gazing at any object with a frequency of the object, and performing the authentication based on a corresponding security key when the detected frequency is included in a predetermined range.

In one aspect of the present disclosure, there is provided a user authentication apparatus using movement of a pupil, including: an information storage configured to store security keys corresponding to frequencies of the respective objects; a display configured to display a plurality of objects having the respective security keys to move at corresponding frequencies; a pupil position detector configured to detect a position of the pupil of a user for each time zone; a frequency detector configured to detect a frequency based on the position of the pupil of the user for each time zone detected by the pupil position detector; and a controller configured to recognize a security key corresponding to the frequency detected by the frequency detector based on the security keys corresponding to the respective frequencies stored in the information storage and performing user authentication using at least one recognized security key.

In another aspect of the present disclosure, there is provided a user authentication method using movement of a pupil, including: storing, with an information storage, security keys corresponding to frequencies of the respective objects; displaying, with a display, a plurality of objects having the respective security keys to move at corresponding frequencies; detecting, with a pupil position detector, a position of the pupil of a user for each time zone; detecting, with a frequency detector, a frequency based on the position of the pupil of the user for each time zone detected by the pupil position detector; and recognizing, with a controller, a security key corresponding to the frequency detected by the frequency detector based on the security keys corresponding to the respective frequencies stored in the information storage and performing user authentication using at least one recognized security key.

BRIEF DESCRIPTION OF THE DRAWINGS

The above and other objects, features and advantages of the present disclosure will be more apparent from the following detailed description taken in conjunction with the accompanying drawings, in which.

DETAILED DESCRIPTION

Hereinafter, exemplary embodiments of the present disclosure will be described in detail with reference to the accompanying drawings.

Figure 1:
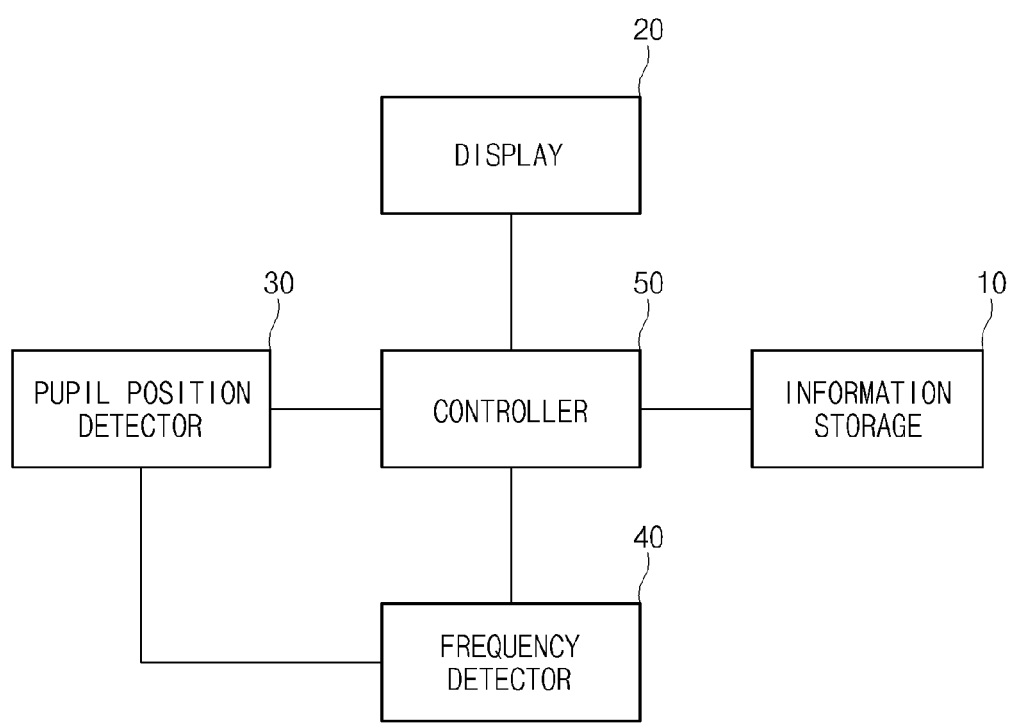
FIG. 1 is a configuration diagram of a user authentication apparatus using movement of a pupil according to an exemplary embodiment of the present disclosure.

FIG. 1 is a configuration diagram of a user authentication apparatus using movement of a pupil according to an exemplary embodiment of the present disclosure.

As shown in FIG. 1, the user authentication apparatus 100 is configured to include an information storage 10, a display 20, a pupil position detector 30, a frequency detector 40, and a controller 50.

Each of the above-mentioned respective units will be described. First, the information storage 10 stores security keys corresponding to frequencies of the respective objects. The respective objects may be matched to a preset frequency, and the respective frequencies matched to the respective security keys.

The display 20 displays the respective objects to move at corresponding frequencies under a control of the controller

50. In some embodiments, a range of the frequency is 0.05 to 5 Hz, and may be derived from movement of a pupil.

Generally, when an object mechanically moves, for example, periodically reciprocates, if a user, such as a driver of a vehicle, gazes at the object, the user's pupil moves similarly with the movement of the object. Therefore, when the movement, and in some cases, the frequency of the respective object is recognized, if the movement of the pupil is detected and a frequency thereof is confirmed, the object that the pupil gazes at may be recognized.

Figure 2A:
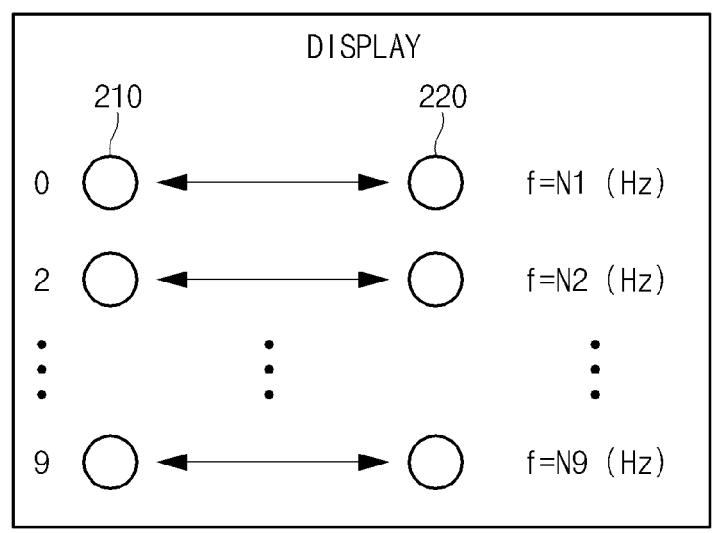
FIGS. 2A to 2C are illustrative views of a scheme of displaying the respective objects so as to have corresponding frequencies.
Figure 2B:
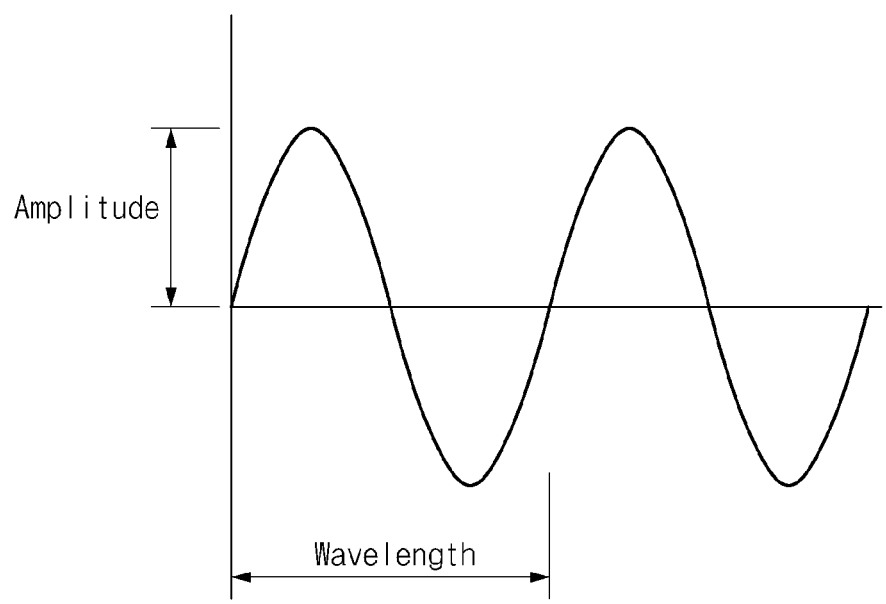
Figure 2C:
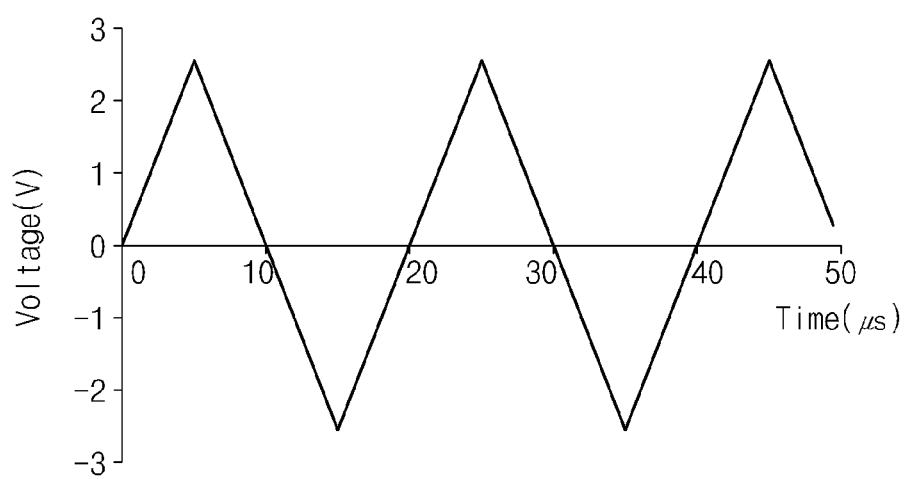

The present disclosure uses the following three schemes as shown in FIGS. 2A to 2C in order to allow an object moving on a screen to have a specific frequency. In some embodiments, there is at least one object moving on the screen.

FIG. 2A shows a scheme of at least one object periodically and alternately display on a screen. As can be seen in FIG. 2A, an object 210 is positioned on a first side of the screen and an object 220 is positioned on a second side on the screen, different than the first side. In this case, the first side of the screen is the left side, and the second side is the right side of the screen. However, the first and second sides may be positioned in various portions of screen as necessary. Therefore, the pupil of the user periodically and alternately gazes at the object 210 positioned at the first side and the object 220 positioned at the second side, such that a frequency may be detected.

In this case, the respective objects on the screen are matched to security keys 0 to 9, respectively. Therefore, the user may gaze at the respective objects to input the security key. For example, when the security key is 5326, the user gazes at the object corresponding to 5, and when an indication indicating that the input has been completed appears, the user gazes at the object corresponding to 3, followed by the object corresponding to 2 and then the object corresponding to 6. 5236 may be input in this scheme.

In another embodiment, the respective objects may have different shapes, such that the shapes themselves may be used as the security keys. For example, a rectangle, a triangle, a lozenge, a circle, a pentagon, a hexagon, an octagon, and the like, may be disposed on the screen so as to have different frequencies, and the user may gaze at corresponding objects in a sequence corresponding to the security keys to allow authentication to be performed.

FIG. 2B shows a scheme of a specific object continuously moving so that the specific object has a form of a sine wave on a screen.

FIG. 2C shows a scheme of a specific object continuously moving so that the specific object has a form of a triangular wave on a screen.

The pupil position detector 30 may detect a position of the pupil of the user for each time zone, that is, movement of the pupil of the user. In some embodiments, the pupil position detector 30 detects the position of the pupil through an 'Adaboost'® algorithm.

As an example, the pupil position detector 30 includes a face area detector, a similarity calculator, and an eye position calculator.

First, the face area detector receives image data, detects face area of the image data, and transfers a face image corresponding to the face area to the similarity calculator.

Then, the similarity calculator calculates pupil similarity using the face image transferred from the face area detector and a pupil descriptor.

In addition, the similarity calculator may calculate a pixel corresponding to the position of the pupil in the pupil similarity based on the entire probability. The pupil descriptor may be stored in a database.

Then, the pupil position calculator calculates a geometrical position of the pupil, for example, a three-dimensional coordinate of the pupil, at a point at which the pupil of the user is actually positioned using a point at which the pixel corresponding to the position of the pupil calculated by the similarity calculator is included. That is, the pupil position calculator may calculate the geometrical position of the pupil using an angle from a camera toward both pupils, a distance between both pupils, and the like. In addition, the pupil position calculator outputs pupil position data on the calculated actual geometrical position of the pupil.

The frequency detector 40 may detect a frequency based on the position of the pupil for each time zone detected by the pupil position detector 30. For example, the frequency detector 40 may detect a peak value between 0.05 and 5 Hz except for a direct current (DC) component in the movement of the pupil using unequally spaced fast Fourier transform (FFT).

The controller 50 may control the display 20 so that the respective objects moving on the screen have predetermined frequencies.

In addition, the controller 50 may control the frequency detector 40 to detect the frequency based on the position of the pupil for each time zone detected by the pupil position detector 30.

In addition, the controller 50 may recognize a security key corresponding to the frequency detected by the frequency detector 40 based on the security keys corresponding to the respective frequencies stored in the information storage 10 and perform user authentication using at least one recognized security key. That is, the controller 50 may perform the user authentication based on the security key corresponding to the frequency detected from the movement of the pupil.

The present disclosure as described above may be applied to all devices requiring the user authentication, such as an automated teller machine (ATM), a cellular phone, and the like. In the case in which the present disclosure is applied, there is an advantage that the authentication may be performed by inputting the security key only by a frequency detection process according to the movement of the pupil.

Figure 3:
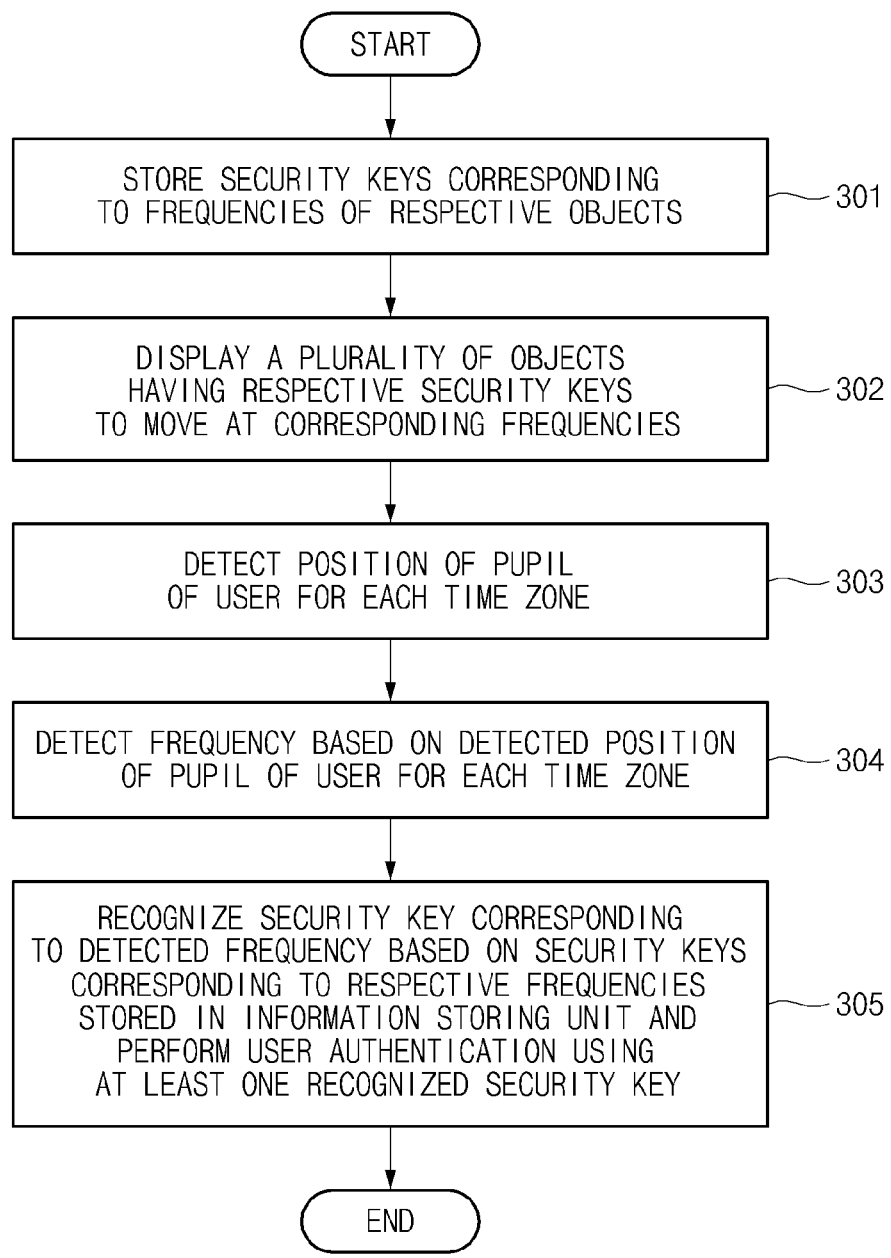
FIG. 3 is a flow chart of a user authentication method using movement of a pupil according to the exemplary embodiment of the present disclosure.

FIG. 3 is a flow chart of a user authentication method using movement of a pupil according to the exemplary embodiment of the present disclosure.

First, the information storage 10 stores the security keys corresponding to the frequencies of the respective objects (301).

Then, the display 20 displays the respective objects to move at corresponding frequencies (302). In this case, the display may display both of the respective objects and the security keys corresponding thereto to allow the user to input the security key in a non-contact scheme. For example, as the user gazes at an object on the screen, the pupil of the user moves according to the movement of the object.

Then, the pupil position detector 30 may detect the position of the pupil for each time zone (303).

Next, the frequency detector 40 may detect a frequency based on the position of the pupil for each time zone detected by the pupil position detector 30 (304).

Thereafter, the controller 50 may recognize a security key corresponding to the frequency detected by the frequency detector 40 based on the security keys corresponding to the respective frequencies stored in the information storage 10 and performs the authentication using at least one recognized security key (305).

As set forth above, according to the exemplary embodiment of the present disclosure, the respective frequencies of objects mechanically moving on the screen and the security keys corresponding thereto are stored, a frequency detected from movement of a pupil gazing at any object is compared with a frequency of the object, and the authentication is performed based on a corresponding security key when the detected frequency is included in a predetermined range, thereby making it possible to rapidly and accurately perform authentication with high security.

What is claimed is:

1. A user authentication apparatus using movement of a pupil, comprising:
   an information storage configured to store security keys corresponding to frequencies of a plurality of respective objects;
   a display configured to display more than one object having the respective security keys to move at corresponding frequencies;
   a processor configured to detect a position of the pupil of a user for at least one time zone; to detect a frequency based on the detected position of the pupil of the user for each time zone; and to recognize a security key corresponding to the detected frequency based on the security keys corresponding to the respective frequencies stored in the information storage and perform user authentication using at least one recognized security key.

2. The user authentication apparatus according to claim 1, wherein the processor is configured to control the display so that the objects periodically and alternately appear at a first side and at a second side different than the first side on a screen.

3. The user authentication apparatus according to claim 1, wherein the processor is configured to control the display so that movement of the object on a screen has a sine wave.

4. The user authentication apparatus according to claim 1, wherein the processor is configured to control the display so that movement of the object on a screen has a triangular wave.

5. The user authentication apparatus according to claim 1, wherein the processor controls the display such that at least one object on a screen has a corresponding frequency.

6. A user authentication method using movement of a pupil, comprising:
   storing, with an information storage, security keys corresponding to frequencies of the respective objects;
   displaying, with a display, more than one object having the respective security keys to move at corresponding frequencies;
   detecting, with a processor, a position of the pupil of a user for each time zone;
   detecting, with the processor, a frequency based on the detected position of the pupil of the user for each time zone; and
   recognizing, with the processor, a security key corresponding to the detected frequency based on the security keys corresponding to the respective frequencies stored in the information storage and performing user authentication using at least one recognized security key.

7. The user authentication method according to claim 6, wherein in the displaying, the objects are displayed so that the objects periodically and alternately appear at a first side and at a second side different than the first side on a screen.

8. The user authentication method according to claim 6, wherein in the displaying, the objects are displayed so that movement of the object on a screen has a form of a sine wave.

9. The user authentication method according to claim 6, wherein in the displaying, the objects are displayed so that movement of the object on a screen has a form of a triangular wave.

* * * * *